United States Patent
Bell et al.

(10) Patent No.: US 10,472,793 B2
(45) Date of Patent: Nov. 12, 2019

(54) METHOD OF MONITORING SUBSURFACE CONCRETE STRUCTURES

(71) Applicants: CEMENTATION SKANSKA LIMITED, Hertfordshire (GB); Cambridge Enterprise Limited, Cambridge (GB); Ove Arup & Partners International Limited, London (GB)

(72) Inventors: Andrew Bell, Doncaster (GB); Yue Ouyang, Doncaster (GB); Kenichi Soga, Cambridge (GB); Duncan Nicholson, London (GB)

(73) Assignees: CEMENTATION SKANSKA LIMITED, Hertfordshire (GB); Ove Arup & Partners International Limited, London (GB); Cambridge Enterprise Limited, Cambridge (GB)

( * ) Notice: Subject to any disclaimer, the term of this patent is extended or adjusted under 35 U.S.C. 154(b) by 145 days.

(21) Appl. No.: 15/117,070

(22) PCT Filed: Feb. 5, 2015

(86) PCT No.: PCT/GB2015/050321
§ 371 (c)(1),
(2) Date: Aug. 5, 2016

(87) PCT Pub. No.: WO2015/118333
PCT Pub. Date: Aug. 13, 2015

(65) Prior Publication Data
US 2017/0067222 A1    Mar. 9, 2017

(30) Foreign Application Priority Data

Feb. 5, 2014 (GB) .................................. 1401921
Feb. 21, 2014 (GB) ................................ 1403124.9

(51) Int. Cl.
*E02D 33/00*     (2006.01)
*E21B 47/00*     (2012.01)
(Continued)

(52) U.S. Cl.
CPC .............. *E02D 33/00* (2013.01); *E02D 5/18* (2013.01); *E02D 5/22* (2013.01); *E02D 15/04* (2013.01);
(Continued)

(58) Field of Classification Search
CPC .. E02D 33/00; E02D 5/18; E02D 5/22; E02D 15/04; G01K 11/32; G01N 21/431;
(Continued)

(56) References Cited

U.S. PATENT DOCUMENTS 5,397,891 A * 3/1995 Udd ................... G01D 5/35312
 250/227.18
7,542,856 B2 * 6/2009 Kishida ................. G01B 11/16
 702/35

(Continued)

FOREIGN PATENT DOCUMENTS

EP        2466063 A1    6/2012
JP        H10-66945 A   3/1998
(Continued)

OTHER PUBLICATIONS

International Search Report issued in PCT/GB2015/050321 dated Jul. 2, 2015 (2 pages).
(Continued)

*Primary Examiner* — Lisa M Caputo
*Assistant Examiner* — Philip L Cotey
(74) *Attorney, Agent, or Firm* — Osha Liang LLP

(57) ABSTRACT

Fiber optic sensors are used to monitor the integrity of a subsurface concrete structure such as a pile or diaphragm wall. A fiber optic sensor array (48) is attached to a rein-
(Continued)

forcement or framework assembly (20) for the subsurface concrete structure. Concrete is applied to surround the reinforcement or framework assembly (20) and fiber optic sensor array (48). The fiber optic sensor array (48) is then used to collect temperature data during hydration of the subsurface concrete structure. The temperature data is monitored in real time to determine differentials across the structure, indicative of a problem within the structure.

17 Claims, 4 Drawing Sheets

(51) Int. Cl.

| | | |
|---|---|---|
| E21B 47/12 | (2012.01) | |
| G01N 33/38 | (2006.01) | |
| G01K 11/32 | (2006.01) | |
| E21B 33/14 | (2006.01) | |
| G01N 21/43 | (2006.01) | |
| E02D 5/18 | (2006.01) | |
| E02D 5/22 | (2006.01) | |
| E02D 15/04 | (2006.01) | |
| G01V 9/00 | (2006.01) | |

(52) U.S. Cl.
CPC .......... *E21B 33/14* (2013.01); *E21B 47/0005* (2013.01); *E21B 47/123* (2013.01); *G01K 11/32* (2013.01); *G01N 21/431* (2013.01); *G01N 33/383* (2013.01); *G01V 9/005* (2013.01)

(58) Field of Classification Search
CPC ........ G01N 33/383; G01V 9/005; G02B 6/00; E21B 33/14; E21B 47/0005; E21B 47/123
See application file for complete search history.

(56) References Cited

U.S. PATENT DOCUMENTS

| | | | | |
|---|---|---|---|---|
| 9,880,048 | B2* | 1/2018 | Martin | G01D 5/35361 |
| 9,977,008 | B2* | 5/2018 | England | G01N 33/383 |
| 2005/0013342 | A1* | 1/2005 | Kaminski | G01K 11/32 |
| | | | | 374/152 |
| 2007/0058898 | A1 | 3/2007 | Slade et al. | |
| 2007/0065071 | A1* | 3/2007 | Slade | G01D 5/35303 |
| | | | | 385/12 |
| 2007/0116402 | A1* | 5/2007 | Slade | G01N 21/7703 |
| | | | | 385/12 |
| 2010/0281985 | A1* | 11/2010 | Kumagai | G01H 9/004 |
| | | | | 73/655 |
| 2011/0200068 | A1* | 8/2011 | Piscsalko | G01K 1/026 |
| | | | | 374/152 |
| 2012/0205103 | A1 | 8/2012 | Ravi et al. | |
| 2012/0300807 | A1* | 11/2012 | Freitag | G01D 5/353 |
| | | | | 374/161 |
| 2013/0271769 | A1* | 10/2013 | Handerek | E21B 47/06 |
| | | | | 356/446 |
| 2013/0286378 | A1* | 10/2013 | Dutoit | E21B 47/0001 |
| | | | | 356/32 |
| 2013/0341497 | A1* | 12/2013 | Zuardy | G01D 5/35358 |
| | | | | 250/227.14 |
| 2015/0276702 | A1* | 10/2015 | England | G01N 33/383 |
| | | | | 374/4 |

FOREIGN PATENT DOCUMENTS

| | | |
|---|---|---|
| KR | 10-2010-0116365 A | 11/2010 |
| WO | 2012/076935 A1 | 6/2012 |

OTHER PUBLICATIONS

Written Opinion of the International Searching Authority issued in PCT/GB2015/050321 dated Jul. 2, 2015 (6 pages).
Combined Search and Examination Report for corresponding United Kingdom Application No. GB1501947.4, dated Jul. 24, 2015 (7 pages).
Glisic, B. et al.; "Monitoring of Early and Very Early Age Deformation of Concrete Using Fiber Optic Sensors"; Federation Internationale du Beton, Proceedings of the 2nd International Congreess, Jun. 5-8, 2006, Naples, Italy (12 pages).
Combined Search and Examination Report for corresponding United Kingdom Application No. GB1401921.0, dated Aug. 1, 2014 (6 pages).
Bellountou, E-A et al. "Thermal Integrity Profiling: A Recent Technological Advancement in Integrity Evaluation of Concrete Piles," Proceedings From the First International Conference, Seminar on Deep Foundations; Santa Cruz, Bolivia; Apr. 23, 2013 (Apr. 23, 2013), pp. 1-20, XP002743515.
Wang, Yong "Monitoring of concrete curing process with embedded fiber Bragg gratings," Proceedings of SPIE, vol. 1204, Jan. 1, 2001 (Jan. 1, 2001), pp. 23-30, XP055005138, ISSN: 0277-786X, DOI 10.1 1 1711 2.41 7409.
Mullins, Gray et al. "Thermal Integrity Profiling: An Innovative Technique for Drilled Shafts Special Issue: Innovation," Deep Foundations May/Jun. 2012, May 2, 2012 (May 2, 2012), pp. 51-54, XP055388918, Retrieved from the Internet: URL:http://www.grlengineers.com/wp-content/uploads/2012/05/ DFI_MAY_JUN2012_pg51-54.pdf [retrieved on Jul. 7, 2017].
Examination Report issued in corresponding EP Application No. 15710836.6 dated Feb. 21, 2018 (3 pages).

* cited by examiner

METHOD OF MONITORING SUBSURFACE CONCRETE STRUCTURES

BACKGROUND

There is a need to minimise failures within the built environment. In recent years, this has been driven not only by safety considerations, but also by a need to optimise the use of limited natural resources.

As such, it is necessary to monitor built structures, in order to identify potential failures. A problem arises when the built structure is inaccessible, e.g. if the structure is at a subsurface location.

Subsurface concrete structures are generally made by pouring fresh concrete into a cavity (such as an underground borehole, or a shuttered structure to contain the concrete). They require non-visual assessment after curing to ensure that the poured concrete is present in the designed quantity at all points in the structure and that there are no voids, bulges or significant anomalies in the concrete.

In some cases, strain gauges are used to facilitate non-visual assessment of subsurface structures after curing. The non-visual assessment of subsurface structures after curing may also be done using a technique known as cross-hole sonic logging.

However, in the case of subsurface structures made from concrete poured in situ, a potential failure may arise during the construction of the structure. There is therefore a need to identify potential failures as early as possible, particularly in those subsurface structures that are used to support or retain other structures, such as concrete piles or diaphragm walls.

SUMMARY OF THE DISCLOSURE

The present invention relates to a method of monitoring subsurface concrete structures, in particular a method of monitoring subsurface concrete structures during hydration of the concrete.

According to a first aspect, there is provided a method of monitoring a subsurface concrete structure, the method including the steps of:
providing a reinforcement or framework assembly for a subsurface concrete structure;
providing a fibre optic array in association with the reinforcement or framework assembly;
installing the reinforcement or framework assembly at a desired subsurface location;
applying concrete medium to surround the reinforcement or framework assembly and fibre optic array at the subsurface location;
using the fibre optic array immediately or shortly after the application of said concrete medium to directly sense and collect temperature data during hydration of the subsurface concrete structure; and
analysing the temperature data to determine a characteristic of the subsurface concrete structure.

The term 'subsurface concrete structure' is intended to mean a concrete structure having at least a significant part of the structure located below ground level, e.g. in a borehole or cavity.

The disclosure allows for real-time temperature monitoring of the structure during hydration of the concrete, thereby providing a mechanism for identifying potential anomalies and defects (e.g. due to the presence of voids, fissures or non-homogeneous concentrations within the structure) during formation and before the structure is completed.

It is highly desirable to ensure that a uniform concrete structure has been formed and that there are no anomalies which will cause the structure to be weak. Concrete defects could be present due to a congested reinforcement, which is difficult to detect. By using methods according to embodiments of the present disclosure, heat generation and dissipation within the concrete during the curing process may be observed, and as a result, potential failures may be detected early.

In addition, methods in accordance with the disclosure may allow for a structure to be instrumented ahead of construction, thus minimising the presence of operators during the placement of the framework or reinforcement assembly and pouring of the concrete medium.

The collecting/gathering of temperature data may be performed on site or remotely. The remote gathering of data is advantageous as it reduces human capital requirements on site.

A fibre optic array may be used to collect distributed temperature data, and the distributed temperature data may be analysed to determine the integrity of the subsurface concrete structure.

An interrogator may be connected to the fibre optic array, for collecting the temperature data during hydration of the subsurface concrete structure. This facilitates the assessment of the temperature data.

The interrogator may also be set up for automatic data collection.

Preferably, the temperature may be monitored in real time during hydration of the subsurface concrete structure. A much more information-rich temperature data set may be produced from real time temperature monitoring methods of the present disclosure, which may enable the assessment of the overall structure thermal condition throughout the curing process, along with clear identification of regions in the structure not exhibiting heat flow—that may be indicative of anomalies within the concrete structure.

A fibre optic array may include at least one fibre optic cable sensor. In exemplary embodiments, the fibre optic array comprises a plurality of fibre optic cable sensors.

In embodiments comprising a plurality of fibre optic cable sensors, preferably each fibre optic cable sensor extends to a known depth within the reinforcement or framework assembly of the subsurface structure.

A fibre optic array may include at least one fibre optic cable sensor in an open loop arrangement having a first section and a second section spaced apart from one another and extending along a length of the reinforcement or framework assembly.

The first section of the at least one fibre optic cable sensor may be arranged on one side of the reinforcement or framework assembly and the second section of said at least one fibre optic cable sensor may be arranged on an opposing side of the reinforcement or framework assembly.

In exemplary embodiments, a first fibre optic cable sensor may be arranged to extend in an open loop along a central axis of the reinforcement or framework assembly.

In exemplary embodiments, one or more additional fibre optic cable sensors may be arranged to each define a single or a plurality of open loops at a peripheral location of the reinforcement or framework assembly.

One or more or each fibre optic cable sensor may be attached to the reinforcement or framework assembly prior to location of the reinforcement or framework assembly at the subsurface location.

One or more or each fibre optic cable sensor may be a single mode fibre optic sensor or a multimode fibre optic sensor.

The installation of the components for monitoring the integrity of the concrete structure using one or more methods in accordance with the disclosure is efficient and safe, which are important factors on an active construction site.

BRIEF DESCRIPTION OF DRAWINGS

Other aspects and features of the disclosure will be apparent from the following description, made by way of example, with reference to the following drawings.

DETAILED DESCRIPTION

Figure 1:
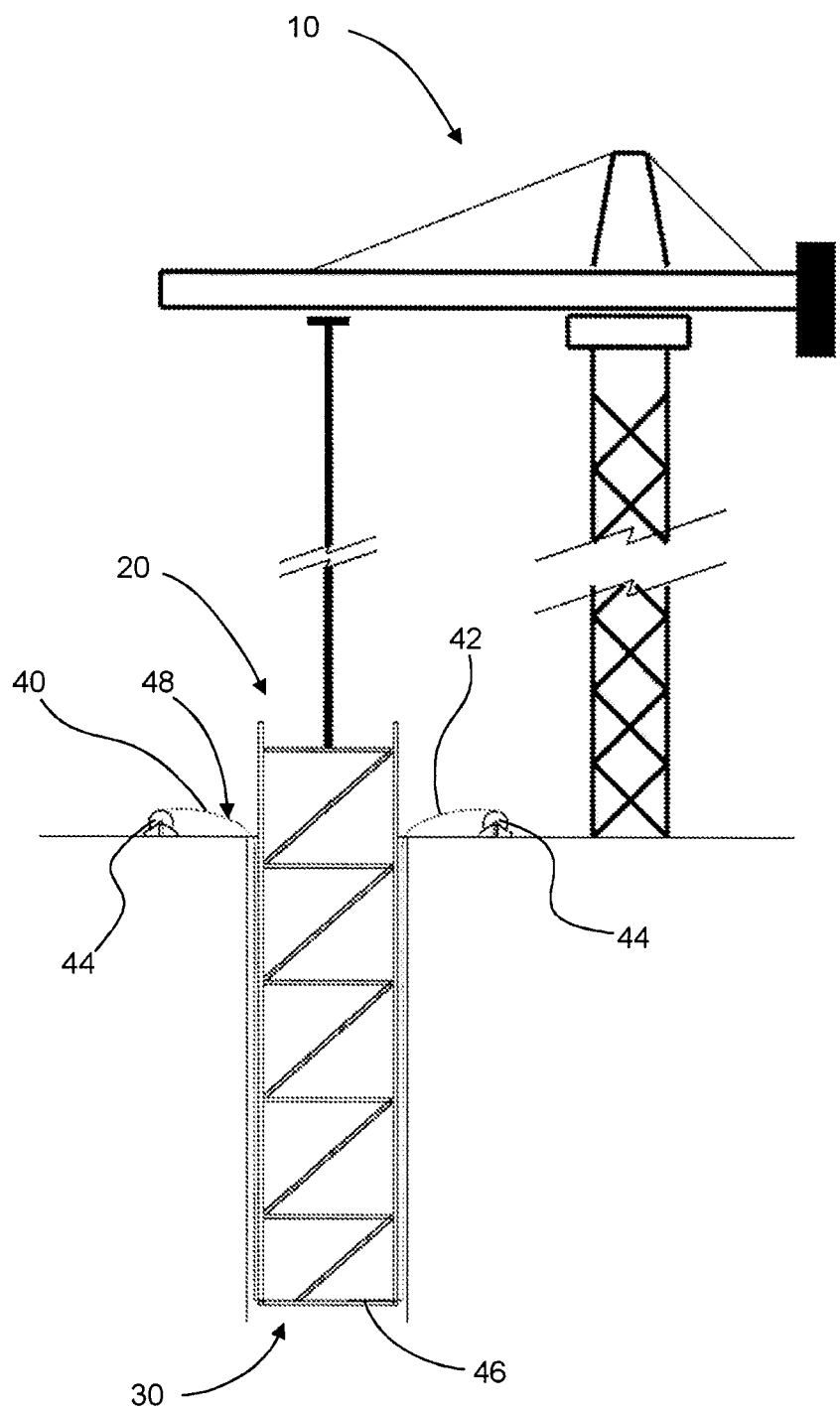
FIG. 1 is a schematic diagram showing one stage of a method of installation of a subsurface concrete structure.

Referring firstly to FIG. 1, a crane or other suitable lifting device 10 is shown lowering a reinforcement or framework assembly 20 into a borehole or cavity 30 in the ground, for the purpose of creating a subsurface concrete structure.

Once the assembly 20 has been positioned at the desired location, concrete (not shown) is applied to fill the borehole or cavity 30, thereby surrounding the assembly 20.

In an alternative method, the concrete may be placed first, with the assembly 20 then placed into the wet concrete.

As will be understood, the concrete will undergo a period of hydration, during which the concrete will harden to create a subsurface concrete structure having integral reinforcement or framework.

The reinforcement or framework assembly 20 (hereinafter referred to as 'the assembly') is configured to define a substructure of the subsurface concrete structure to be created. As such, the assembly 20 may typically be constructed as a cage or frame, using metal bar or the like. According to a preferred method of the invention, the assembly 20 may be constructed above ground (e.g. on site or at a location remote from the intended installation location).

In exemplary embodiments, the assembly 20 may be configured for creating a concrete pile or panel of a diaphragm wall, for example.

In general terms, a fibre optic array may be used to directly sense and collect temperature data during hydration of the subsurface concrete structure. That is to say, the fibre optic array may function as a temperature sensor array. This is different than known prior art monitoring systems wherein a plurality of discrete sensors are individually positioned at set subsurface locations within the poured concrete.

In the example of FIG. 1, a fibre optic cable sensor 48 is provided in association with the assembly 20. The term "fibre optic cable sensor" is used to indicate a fibre optic cable in which the optical fibre acts as a sensing element. The fibre optic cable sensor 48 is arranged in an open loop (i.e. folded/turned or doubled upon itself so as to leave an opening between its parts) having two sections (a first section and a second section) 40, 42 which are spaced apart from one another, with the first section 40 of the fibre optic cable sensor 48 extending down one side of the assembly 20 and the second section 42 of the fibre optic cable sensor 48 extending up from the opposing side of the assembly 20. A third section 46 of the fibre optic cable sensor 48 connecting the first and second sections extends across an underside of the assembly 20. The fibre optic cable sensor 48 is attached to the assembly 20 (e.g. using an adhesive, clamps, twisted wire, clips or ties or the like), prior to location at said subsurface location. For example, the fibre optic cable sensor is attached above ground, during or after construction of the assembly 20.

In the illustrated example of FIG. 1, rollers 44 are used to guide the fibre optic cable sensor 48 during the lowering of the assembly 20 into the borehole or cavity 30. It would be understood that where rollers 44 are used, the first and second sections 40, 42 of the fibre optic cable sensor 48 may be attached to the respective side of the assembly 20 as it is being lowered into the cavity 30.

The fibre optic cable sensor 48 may be a conventional single mode optical fibre sensor e.g. of a kind known in the art or a multimode optical fibre sensor.

Figure 2:
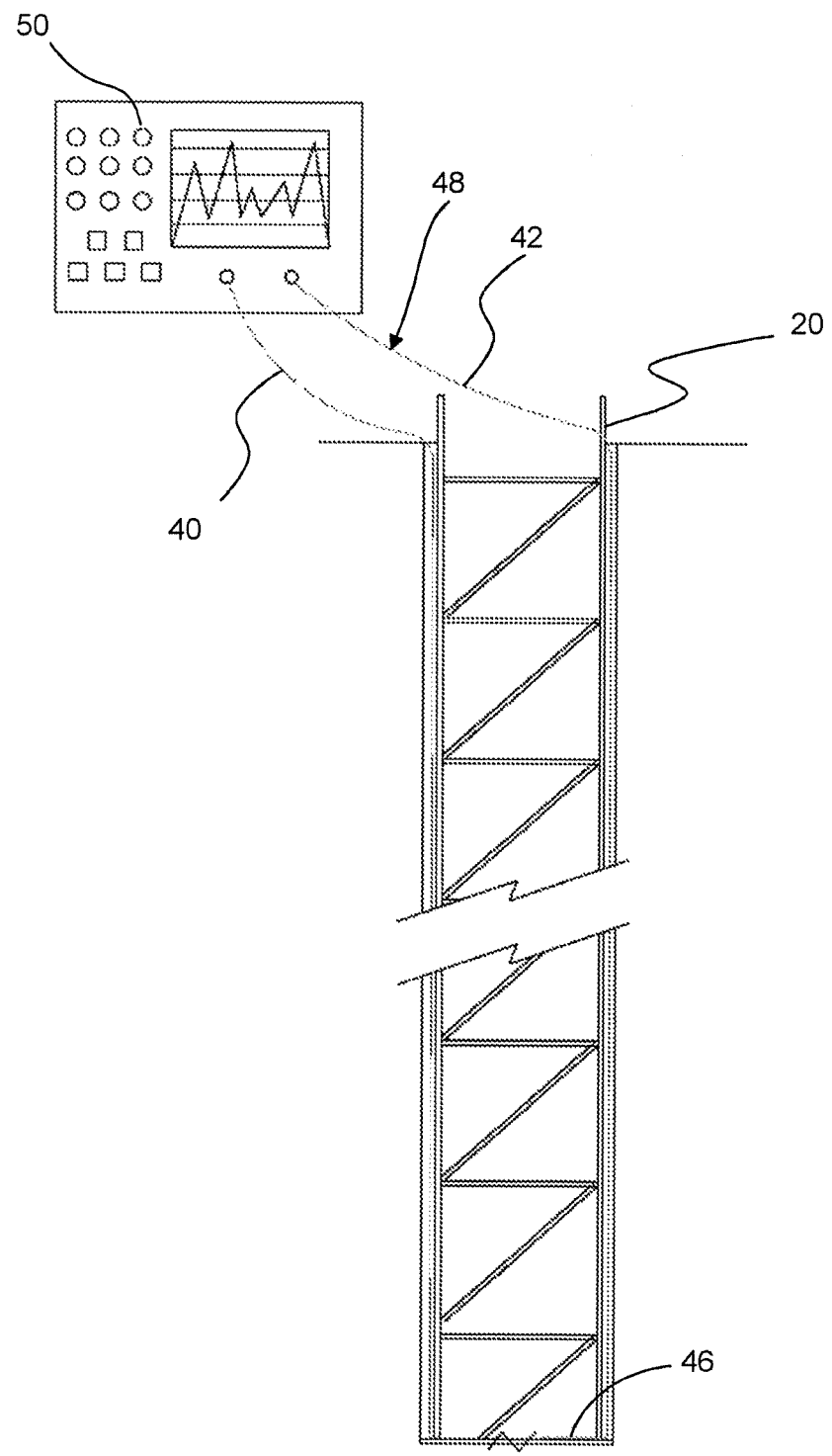
FIG. 2 is a schematic diagram showing a further stage of a method of installation of a subsurface concrete structure.

As can be seen in FIG. 2, an interrogator 50 is connected to each section 40, 42 of the fibre optic cable sensor 48, preferably before the assembly 20 is immersed in concrete. The fibre optic cable sensor 48 also functions as a communication link to the interrogator 50. The interrogator 50 is configured to collect the measured temperature data from the first and second sections 40, 42 of the fibre optic cable sensor 48 during hydration of the subsurface concrete structure.

In exemplary embodiments, the collected temperature data may be used for determining one or more characteristics of the subsurface concrete structure. More particularly, the data may be monitored to determine the integrity of the subsurface concrete structure, thus identifying potential anomalies within the subsurface concrete structure. For example, during hydration, a pattern of changes in the spatially distributed temperature may be anticipated along the structure, and if the collected data varies significantly from the anticipated pattern, this will indicate an anomaly within the structure (e.g. a void, fissure or non-homogeneous concentration of material). The spatially distributed temperature data can then be interrogated to identify the location of the anomaly.

In exemplary methods, a single fibre optic cable sensor may be used to collect the temperature data. In the embodiment of FIG. 2, the first and second sections 40, 42 of the fibre optic cable sensor 48 are used for detecting undesired temperature differentials across the hydrating structure (e.g. by comparing the temperature at one side with the temperature at the other side, for any given depth below ground level). In other embodiments, any number of fibre optic cable sensors could be used.

In exemplary methods, a first fibre optic cable sensor may be arranged to extend in an open loop along a central axis of the assembly 20, and one or more additional fibre optic cable sensors may be arranged to each define a single or a plurality of open loops at peripheral locations of the assembly 20 (e.g. spaced circumferentially with respect to the periphery of the structure).

Figure 3:
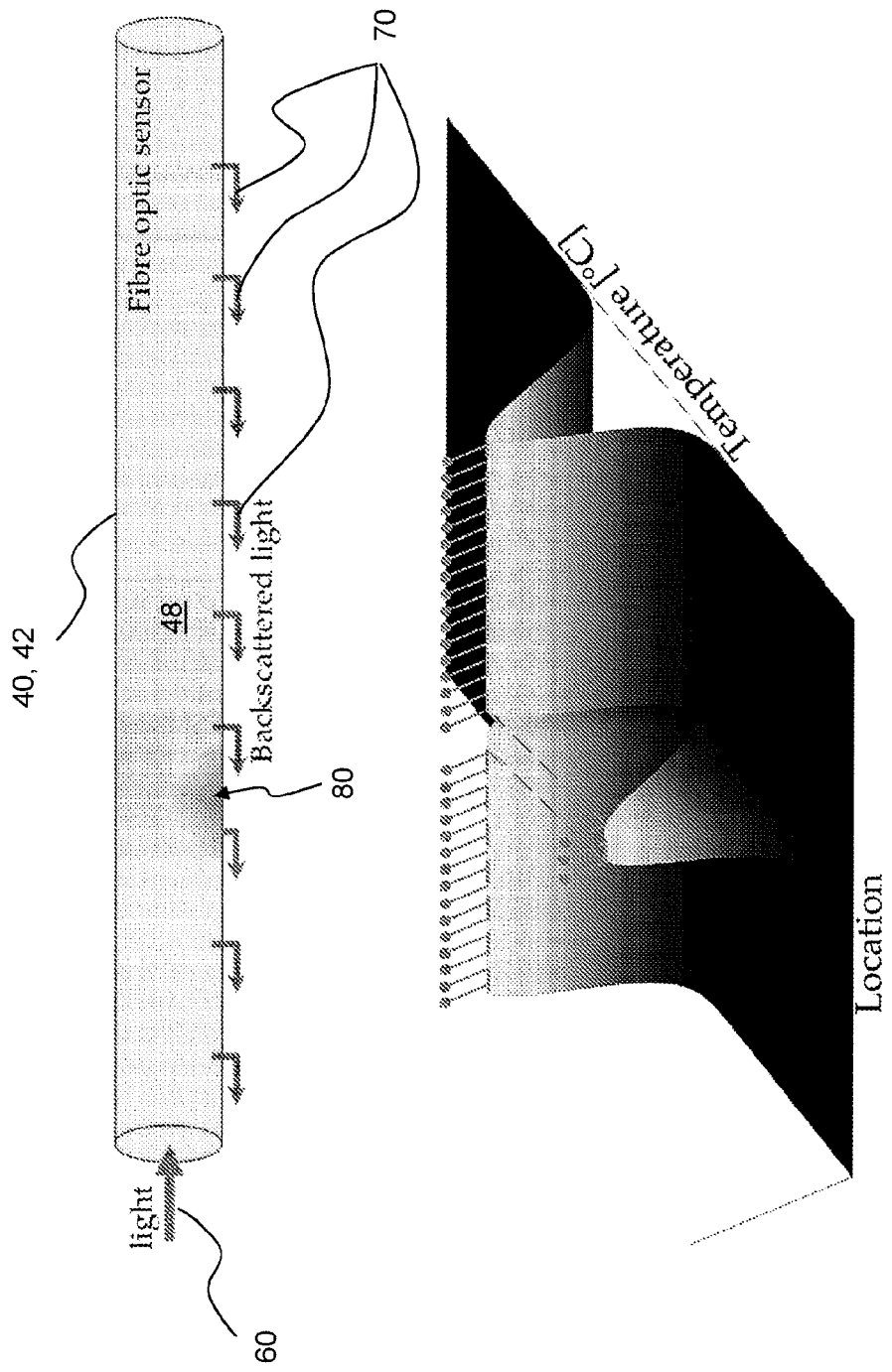
FIG. 3 is a schematic diagram showing an example of the dynamic temperature data sensed and collected by the optical fibre array during hydration of the subsurface concrete structure.

With particular reference to FIG. 3, an exemplary method of directly sensing and collecting temperature data during hydration of the subsurface concrete structure will be described.

As mentioned above, the concrete will undergo a period of hydration, during which the concrete will harden to create a subsurface concrete structure having integral reinforcement or framework.

At the start of the hydration period and throughout the hydration period, a light signal 60 is transmitted down the fibre optic cable sensor 48.

As the light signal 60 is transmitted down the fibre optic cable sensor 48, temperature data in the form of back-scattered signals 70 are collected by the interrogator 50 along the length of the fibre optic cable sensor 48. In exemplary methods, the light signal 60 is in the form of a laser signal.

The collected back-scattered signals 70 are reconstructed into visual form, for example, in the form of a graph as shown in FIG. 3, in order to determine one or more characteristics of the subsurface concrete structure.

The temperature data is averaged over a prescribed length and sampled at a prescribed rate. For example, the temperature data may be averaged over a length of 0.5 m every 0.05 m along the length of the fibre optic cable sensor 48. This provides a distributed measurement of the temperature data by the fibre optic cable sensor 48 across the length of the hydrating concrete, rather than discrete spaced apart measurements at different positions in the hydrating concrete as currently obtained by methods known in the art. Accordingly, the risk of bypassing or not identifying a location of potential failure, as may be the case in the prior art methods if the location occurs between two discrete sensors positions, is significantly reduced.

A region 80 with poor heat flow, which is indicative of an anomaly, may be indicated by a change in the spatially distributed temperature profile.

In exemplary embodiments, the temperature data is monitored in real time during hydration of the subsurface concrete structure. The real time monitoring of temperature data for the structure during hydration of the concrete may provide a mechanism for identifying potential failures (e.g. due to the presence of voids, fissures or non-homogeneous concentrations within the structure) before the structure is completed.

Although described with reference to concrete piles and diaphragm walls, the method is also applicable to other subsurface concrete structures, such as raft foundations etc.

While the fibre optic cable sensor is shown in FIG. 2 as having a single open loop, it would be understood that the sensor may be arranged to define a plurality of open loops with each open loop having a downward extending section and an upward extending section. An example, of such an arrangement is shown in FIGS. 4 and 5.

Figures 4, 5:
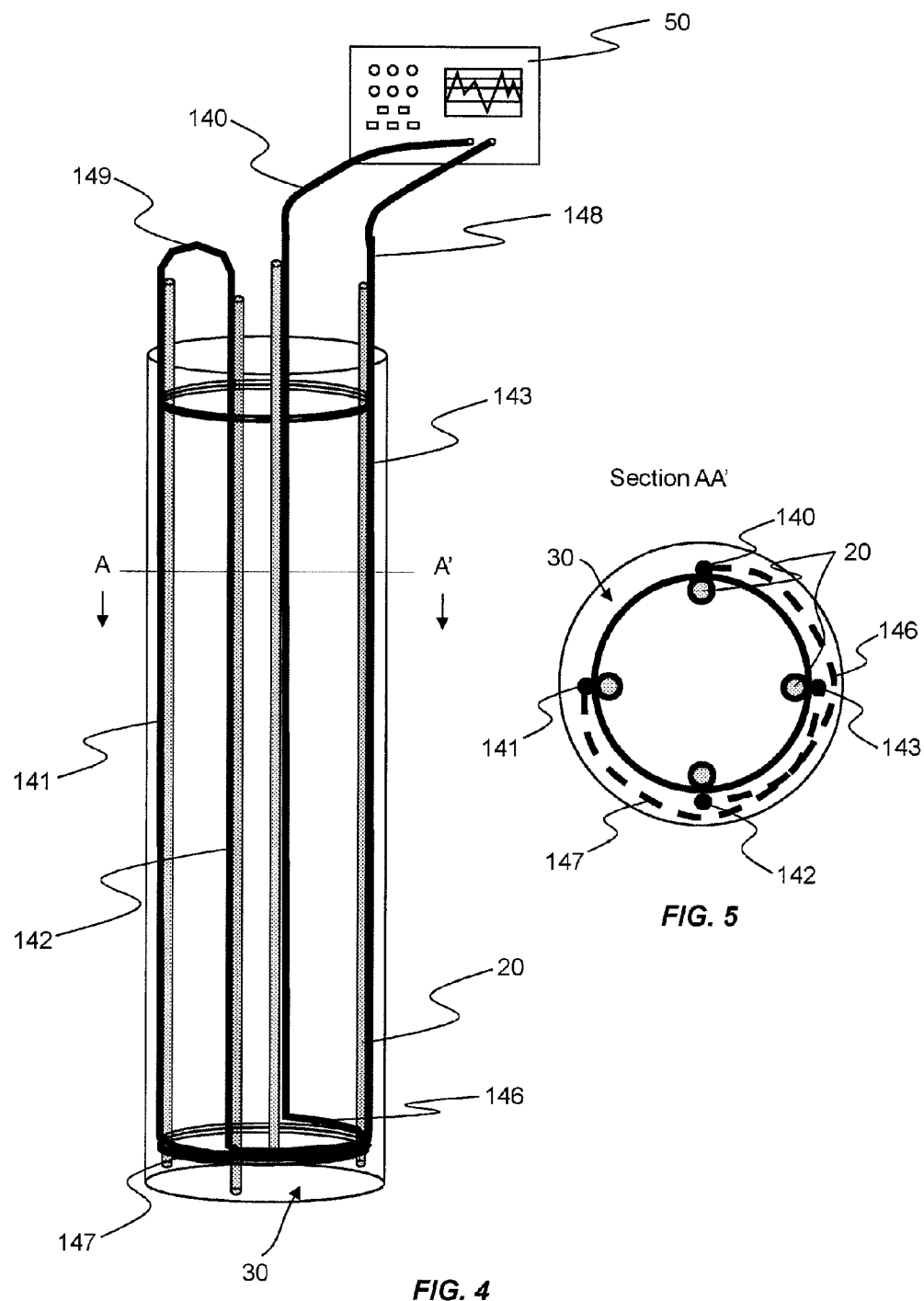
FIG. 4 is a schematic diagram showing an exemplary arrangement of an optical fibre array positioned on a reinforcement assembly in a borehole.
FIG. 5 is a cross-sectional view of the borehole along AA' in FIG. 4.

In the embodiment shown in FIGS. 4 and 5, the fibre optic cable sensor 148 is arranged to define two open loops. The first loop is defined by a first section 140 of the fibre optic cable sensor 148 extending down one side of the assembly 20, a second section 142 of the fibre optic cable sensor 148 extending up from a diametrically opposite side of the assembly 20, and a third section 146 of the fibre optic cable sensor 148 connecting the first and second sections 140, 142. In the embodiment shown, the third section 146 extends along an outer perimeter of the assembly (see FIG. 5), although it would be understood that it may extend across an underside of the assembly 20 as in the previously described embodiment.

The second loop is defined by a fourth section 141 of the fibre optic cable sensor 148 extending down a third side of the assembly 20, a fifth section 143 of the fibre optic cable sensor 148 extending up from a fourth side of the reinforcement assembly 20 diametrically opposite the third side, and a sixth section 147 of the fibre optic cable sensor 148 connecting the fourth and fifth sections 141, 143. A seventh section 149 of the fibre optic cable sensor 148 connects the second section 142 to the fourth section 141.

The number of loops and hence the number of sections of the fibre optic cable extending along the sides of the assembly and their relative spacing may be decided by the desired spatial resolution of temperature measurement. The temporal and spatial temperature profile evaluated from the fibre optic cable sensor readings may be used for data interpretation.

For example, for a circular cross-sectional concrete column of diameter 0.6 m, and perimeter 3.77 m, having four vertical fibre optic cable sections along its length would allow a peripheral spatial resolution of less than 1 m.

Although the invention has been described above with reference to one or more preferred embodiments, it will be appreciated that various changes or modifications may be made without departing from the scope of the invention as defined in the appended claims.

The invention claimed is:

1. A method of monitoring a subsurface concrete structure, the method comprising:
   providing a reinforcement or framework assembly for a subsurface concrete structure;
   providing a fibre optic array in association with the reinforcement or framework assembly, the fibre optic array comprising at least one fibre optic cable sensor, wherein the fibre optic cable sensor comprises a fibre optic cable which acts as a sensing element;
   installing the reinforcement or framework assembly at a desired subsurface location;
   applying concrete medium to surround the reinforcement or framework assembly and the at least one fibre optic cable sensor at the subsurface location;
   using the at least one fibre optic cable sensor immediately or shortly after the application of concrete medium to directly sense and collect temperature data along a length of the at least one fibre optic cable sensor during hydration of the subsurface concrete structure; and
   analysing the temperature data to determine a characteristic of the subsurface concrete structure,
   wherein the at least one fibre optic cable sensor is folded upon itself so as to leave an opening between its parts, thereby forming an open loop arrangement having a first section and a second section spaced apart from one another and extending along a length of the reinforcement or framework assembly.

2. The method of claim 1, wherein providing the reinforcement or framework assembly comprises providing a reinforcement cage for the subsurface concrete structure.

3. The method of claim 2, wherein the at least one fibre optic cable sensor is attached to the reinforcement cage prior to location of the reinforcement cage at the subsurface location.

4. The method of claim 1, wherein the fibre optic array is used to collect spatially distributed temperature data, and the distributed temperature data is analysed to determine the integrity of the subsurface concrete structure.

5. The method of claim 1, wherein an interrogator is connected to the fibre optic array for collecting the temperature data during hydration of the subsurface concrete structure.

6. The method of claim 1, wherein the temperature data is monitored in real time during hydration of the subsurface concrete structure.

7. The method of claim 1, wherein each fibre optic cable sensor extends to a known depth within the reinforcement or framework assembly of the subsurface structure.

8. The method of claim 1, wherein the first section of the at least one fibre optic cable sensor is arranged on one side of the reinforcement or framework assembly and the second section of the at least one fibre optic cable sensor is arranged on an opposing side of the reinforcement or framework assembly.

9. The method of claim 1, wherein a first fibre optic cable sensor is arranged to extend in an open loop along a central axis of the reinforcement or framework assembly.

10. The method of claim 1, wherein one or more additional fibre optic cable sensors are arranged to each define a single or a plurality of open loops at a peripheral location of the reinforcement or framework assembly.

11. The method of claim 1, wherein the at least one optic cable sensor is a single mode fibre optic sensor or a multimode fibre optic sensor.

12. The method of claim 1 wherein the subsurface structure is a concrete pile or diaphragm wall.

13. A reinforcement or framework assembly for a subsurface concrete structure, comprising:
    a cage constructed from at least one metal bar; and
    a fibre optic array attached to the cage, the fibre optic array comprising at least one fibre optic cable sensor, the fibre optic cable sensor comprising a fibre optic cable which acts as a sensing element, the fibre optic cable sensor folded upon itself so as to leave an opening between its parts, thereby forming an open loop arrangement having a first section and a second section spaced apart from one another and which extend along a length of the reinforcement or framework assembly.

14. The reinforcement or framework assembly according to claim 13, wherein the fibre optic array is used to collect spatially distributed temperature data, and the distributed temperature data is analysed to determine the integrity of the subsurface concrete structure.

15. The reinforcement or framework assembly according to claim 13, wherein an interrogator is connected to the fibre optic array for collecting the temperature data during hydration of the subsurface concrete structure.

16. The reinforcement or framework assembly according to claim 13, wherein each fibre optic cable sensor extends to a known depth within the reinforcement or framework assembly of the subsurface structure.

17. The reinforcement or framework assembly according to claim 13, wherein the first section of the at least one fibre optic cable sensor is arranged on one side of the reinforcement or framework assembly and the second section of the at least one fibre optic cable sensor is arranged on an opposing side of the reinforcement or framework assembly.

* * * * *